(12) United States Patent
Luo et al.

(10) Patent No.: US 11,788,047 B2
(45) Date of Patent: Oct. 17, 2023

(54) PARALLEL BIOREACTOR SYSTEM

(71) Applicant: Zhejiang Jinyishengshi Bioengineering Co., Ltd, Zhejiang (CN)

(72) Inventors: Shun Luo, Huzhou (CN); Fulin Hu, Huzhou (CN); Shiping Yuan, Huzhou (CN); Jinpei Song, Huzhou (CN)

(73) Assignee: Zhejiang Jinyishengshi Bioengineering Co., Ltd, Huzhou (CN)

( * ) Notice: Subject to any disclaimer, the term of this patent is extended or adjusted under 35 U.S.C. 154(b) by 177 days.

(21) Appl. No.: 17/381,146

(22) Filed: Jul. 20, 2021

(65) Prior Publication Data

US 2021/0348100 A1     Nov. 11, 2021

Related U.S. Application Data

(63) Continuation of application No. 15/391,927, filed on Dec. 28, 2016, now Pat. No. 11,136,541.

(51) Int. Cl.
*C12M 1/00* (2006.01)
*C12M 3/06* (2006.01)
(Continued)

(52) U.S. Cl.
CPC ............ *C12M 23/58* (2013.01); *C12M 23/14* (2013.01); *C12M 23/28* (2013.01); *C12M 23/38* (2013.01);
(Continued)

(58) Field of Classification Search
CPC ...... C12M 23/14; C12M 23/28; C12M 23/38; C12M 23/48; C12M 23/58; C12M 27/16;
(Continued)

(56) References Cited

U.S. PATENT DOCUMENTS

| 4,356,736 A | 11/1982 | Riedl |
| 2010/0076380 A1 | 3/2010 | Hui |

(Continued)

FOREIGN PATENT DOCUMENTS

| WO | WO2006138143 A1 | 12/2006 |
| WO | WO2013186294 A1 | 12/2013 |

*Primary Examiner* — Lydia Edwards
(74) *Attorney, Agent, or Firm* — NZ CARR LAW OFFICE

(57) ABSTRACT

The present invention provides a parallel bioreactor system, comprising: an oscillator for generating oscillating motion; a plurality of culture vessels mounted on the oscillator, wherein each culture vessel is provided with an inner cavity, the inner cavity comprises a cylindrical portion at the upper part and an inverted truncated conical bottom at the lower part, a cross section of the cylindrical portion is consistent with the cross section of the top of the inverted truncated conical bottom, and the bottom of the cylindrical portion is joined with the top of the inverted truncated conical bottom; disposable culture bags arranged in the inner cavities of the culture vessels and used for accommodating culture solution, wherein each disposable culture bag is provided with a multifunctional cover plate, and the multifunctional cover plate is connected to the top of the culture bag to seal the culture bag, and is provided with a plurality of connection holes leading to interior of the disposable culture bag; and a control system, wherein the control system controls the oscillating motion of the oscillator and parameters of the culture solution in the disposable culture bags.

13 Claims, 6 Drawing Sheets

(51) Int. Cl.
*C12M 1/36* (2006.01)
*C12M 1/34* (2006.01)
*C12M 3/00* (2006.01)

(52) U.S. Cl.
CPC ............ *C12M 23/48* (2013.01); *C12M 27/16* (2013.01); *C12M 29/10* (2013.01); *C12M 41/12* (2013.01); *C12M 41/26* (2013.01); *C12M 41/32* (2013.01); *C12M 41/42* (2013.01); *C12M 41/44* (2013.01); *C12M 41/48* (2013.01)

(58) Field of Classification Search
CPC ...... C12M 29/10; C12M 41/12; C12M 41/26; C12M 41/32; C12M 41/42; C12M 41/44; C12M 41/48
See application file for complete search history.

(56) References Cited

U.S. PATENT DOCUMENTS

2010/0190245 A1 7/2010 Hui
2013/0323841 A1 12/2013 Kruglick

PARALLEL BIOREACTOR SYSTEM

CROSS-REFERENCE TO RELATED APPLICATIONS

This application is a continuation the co-pending U.S. patent application Ser. No. 15/391,927, filed on Dec. 28, 2016.

FIELD OF THE INVENTION

The present invention provides a parallel bioreactor system and a culturing method using the parallel bioreactor system.

BACKGROUND OF THE INVENTION

The new generation of protein drugs represented by antibodies has attracted more and more attention because of its advantages of good targeting, high curative effect, few side effects and the like, and it has become the mainstream in the development of biotech drugs internationally. Further, in recent years, as the avian flu, the foot-and-mouth disease, the swine flu and other diseases have wreaked havoc over the world, it is necessary to quickly develop and produce a large number of urgently needed vaccines and related biological protein drug products within a short period. Rapid production of the aforementioned protein drugs, antibodies and vaccine products relies on equipment really capable of implementing the large-scale culture of animal cells, i.e. bioreactors.

Bioreactors are a bridge connecting the laboratory technology research and the scale production in the factory of the vaccines and the protein drug.

In the past, the culturing mainly relates to *E. coli* and yeast systems, which have the advantages of being insensitive to shearing force, having large oxygen consumption and being tolerant to pure oxygen. But membrane protein or secretory protein cannot be expressed in prokaryotic cells, and they do not have functional activity similar to those of natural antibodies, thereby being not the main direction of development.

At present, the sale of animal cell-expressed products accounts for 70% of biological drugs. Mammalian cells have become the most important expression/production system of modern biopharmacy. The only way to realize the large-scale cultivation of animal cells is the bioreactor.

A traditional reactor has three technical factors: oxygen transfer, mixing and control. At present, the main way for oxygen transfer is bubbling, airlift and stirring blade shearing. The main problem of this way is that tension generated by the breakage of bubbles in bubbling and the shearing force of a stirring blade damage the animal cells.

High throughput screening is one of the important technical means in the field of life science and drug innovation, and its core is to get a lot of information through an experiment at a time and find valuable information therein. At the same time, stable and high-expression cell clones/cell strains and its optimized culturing strategies, culturing conditions and culturing technologies are also key factors for efficient and low-cost production of biological drugs.

Compared with traditional stainless steel bioreactors, disposable bioreactors have the advantages of simple operation, stable production process, short preparation time between batches, high production efficiency, no complicated pipelines and other auxiliary facilities, no need of cleaning, disinfection and sterilization, low production cost, easy validation and the like, thereby having been developed and popularized in the development and production of the modern biotechnology drugs and having become the main trend in the development of bioreactors. The currently disclosed or commercially available disposable bioreactors mainly realize the transfer and mixing of all kinds of liquid, gases and other culture media in traditional manner of stirring, bubbling or airlift, which has the shortcomings of high shearing force and large damage to sensitive cells or microorganisms, and thus is not conducive to high-density culture and production. Related prior art includes PCT application (WO 2013/186294) entitled "disposable bioreactor, top plate and related manufacturing method", and the technical solution thereof mainly relates to a disposable bioreactor that can be applied to parallel culture of cells or microorganisms, a top plate thereof and a corresponding manufacturing method. The bioreactor mainly realizes the transfer and mixing of the culture media by stirring and air introduction from the bottom, and a plurality of individual bioreactors are connected in parallel to achieve the parallel control of the entire working process. The solution has the shortcomings that it cannot optimize dissolved oxygen levels for supporting the high-density production of cells, and will lead to differences in culture parameters between groups, thereby being unbeneficial for the high throughput screening of the cell clones and the accurate optimization of the culturing process.

Therefore, there is a need for a multichannel biological culture platform which achieves high throughput screening and/or parallel culture of more than one type of samples while reducing the damage to the sensitive cells or microorganisms.

SUMMARY OF THE INVENTION

According to a preferred embodiment of the present invention, the problem that conventional reactors cannot achieve high throughput screening of samples or cell clones and culture process optimization can be solved. According to a preferred embodiment of the present invention, the problem that conventional high throughput shaking tables cannot achieve microenvironment control in a culture vessel can be solved. According to a preferred embodiment of the present invention, the shearing force is extremely small in the cell culturing, the dissolved oxygen level is high, and the growth density of cells or microorganisms sensitive to the shearing force can be effectively improved, thus providing a great potential of improvement for process optimization and culture medium optimization. According to a preferred embodiment of the present invention, the parallel culture of multiple samples can be carried out at one time under the same external environment and conditions, and the microenvironment in each culture vessel is controllable, thus providing a preferred platform for high throughput screening of the samples, and particularly the high throughput screening of cell clones. According to a preferred embodiment of the present invention, the parallel culture of multiple candidate cell clones can be carried out at one time under the same external environment and conditions, and the microenvironment in each culture vessel is controllable, thus providing a preferred platform for the high throughput screening of stable and high-expression cell clones and culture process optimization. According to a preferred embodiment of the present invention, the parallel culture of one same sample or cell strain can be carried out under the same external environment and conditions, and the microenvironment in each culture vessel is controllable, thus providing a preferred platform for conducting sample/cell culture condition exploration and establishment, culture process optimization, culture medium optimization and accumulation of small amount of sample.

According to the first aspect of the present invention, there is provided a parallel bioreactor system, comprising: an oscillator for generating oscillating motion; a plurality of culture vessels mounted on the oscillator, wherein each culture vessel is provided with an inner cavity, the inner cavity comprises a cylindrical portion at the upper part and an inverted truncated conical bottom at the lower part, a cross section of the cylindrical portion is consistent with the cross section of the top of the inverted truncated conical bottom, and the bottom of the cylindrical portion is joined with the top of the inverted truncated conical bottom; disposable culture bags arranged in the inner cavities of the culture vessels and used for accommodating culture solution, wherein each disposable culture bag is provided with a multifunctional cover plate, and the multifunctional cover plate is connected to the top of the culture bag to seal the culture bag, and is provided with a plurality of connection holes leading to interior of the disposable culture bag; and a control system, wherein the control system controls the oscillating motion of the oscillator and parameters of the culture solution in the disposable culture bags.

Preferably, the disposable culture bag is a flexible culture bag.

Preferably, the flexible culture bag has a shape corresponding to that of the inner cavity of the culture vessel when being unfolded.

Preferably, the outer shape of the culture vessel corresponds to the shape of the inner cavity, and comprises a cylindrical portion at the upper part and an inverted truncated conical bottom at the lower part.

Preferably, the oscillator comprises a support and a shaking plate, the shaking plate generates the oscillating motion relative to the support, and the culture vessels are mounted on the shaking plate.

Preferably, the shaking plate comprises a plurality of culture vessel holes, and each of the culture vessel holes has a shape matched with the outer shape of the culture vessels so as to at least partially accommodate one culture vessel.

Preferably, the culture vessel hole has an inverted truncated conical bottom.

Preferably, the culture holes are structurally distributed in a rectangular array or an annular array.

Preferably, 16 culture vessels are provided and are evenly mounted on the shaking plate in a matrix form of 4 rows and 4 columns.

Preferably, the oscillator is provided with a motor, a main transmission eccentric shaft and supporting eccentric shafts, the main transmission eccentric shaft and the supporting eccentric shafts are connected between the support and the shaking plate by bearings, the motor drives the main transmission eccentric shaft and thus drives the shaking plate to carry out rotary reciprocating horizontal oscillating motion according to a set amplitude. Preferably, the oscillator comprises four supporting eccentric shafts, which are evenly distributed on the bottom of the oscillator, a balancing weight is mounted on each supporting eccentric shaft, and the balancing weight forms an angle of 180° with the eccentric direction to balance a centrifugal force generated by a load in an oscillating process of the oscillator. Preferably, a diameter-height ratio of the inverted truncated conical bottom is greater than 1:1, and the taper angle of the inverted truncated conical bottom is within a range of 30°-70°.

Preferably, each connection hole of the multifunctional cover plate is a thread interface of a unified standard.

Preferably, the connection holes of the multifunctional cover plate are suitable for being connected with a detection electrode or a conduit.

Preferably, 6-12 connection holes are provided.

Preferably, the system further comprising a perfusion system, wherein the perfusion system comprises a bracket having two guide posts and a perfusion type culture bag vessel fixed between the two guide posts, and lifting adjustment buttons are arranged at lower ends of the guide posts.

Preferably, the perfusion type culture bag vessel is connected with the culture vessel through pipelines and the connection holes of the multifunctional cover plate to form an outer circulation type perfusion culture mode.

Preferably, the control system comprises a manual control mode and an automatic control mode.

Preferably, the control system monitors and controls one or more of the following parameters in the disposable culture bag disposed in the culture vessel:liquid level, temperature, pH value and dissolved oxygen level.

Preferably, the control system can independently monitor and control each disposable culture bag.

Preferably, the control system comprises a master control console and a plurality of reaction controllers; the master control console controls the oscillator and is connected to the plurality of reaction controllers to receive data from the plurality of reaction controllers and send a control instruction to the plurality of reaction controllers; and each reaction controller is connected to the corresponding culture vessel to receive the parameters from the culture vessel and carry out related operations on the culture vessel.

Preferably, the plurality of culture vessels are divided into at least two groups, and identical or different cells or microorganisms are cultured in each group of culture vessels.

Preferably, the control system controls the groups of culture vessels to have different culture parameters therebetween.

According to the second aspect of the invention, there is provided a culture method for culturing cells and/or microorganisms by using the parallel bioreactor system of the first aspect of the invention, comprising: independently monitoring and controlling each culture vessel through the control system.

Preferably, the method comprises dividing the plurality of culture vessels into at least two groups, and culturing identical or different cells or microorganisms in each group of culture vessels.

Preferably, the method comprises controlling the groups of culture vessels to have different culture parameters therebetween.

BRIEF DESCRIPTION OF THE DRAWINGS

The accompanying drawings illustrate embodiments of the present invention in an exemplary way without any limitation.

DETAILED DESCRIPTION OF THE EMBODIMENTS

Hereinafter, embodiments of the present invention will be described with reference to the accompany drawings. The following description is merely exemplary and is not intended to limit the protection scope of the present invention.

A parallel bioreactor system according to an embodiment of the present invention is based on a non-bubbling oxygen transfer mechanism, wherein a plurality of culture vessels having inverted truncated conical (inverted frustum of a cone) inner cavities are placed on the same platform (shaking plate or shaking table), and the platform is driven by an oscillator to achieve eccentric oscillating operation. In some embodiments, the parameter control of each culture vessel can be controlled by an independent CPU and actuator(s), records, reports and other data management are relatively independent, and the pH value, dissolved oxygen, nutrients and other parameters in cell culture microenvironments can be accurately regulated and controlled. A disposable culture bag with a matching shape and structure is provided in the culture vessel and is used once being unpacked, so that cross contamination can be avoided, the inter-batch treatment period can be shortened, no washing, disinfection or verification is needed, thus greatly improving the working efficiency. Due to the shape of the inner cavity and the oscillating motion of the culture vessel, the shearing force in the entire cell culture process is extremely small, the dissolved oxygen efficiency is high, the growth density of cells or microorganisms sensitive to the shearing force can be effectively improved, thus providing a great potential improvement for process optimization and culture medium optimization. At the same time, due to the high-level dissolved oxygen efficiency, the oxygen toxicity on the cells by pure oxygen during the high-density growth of the cells or microorganisms can be avoided, and the problems that conventional reactors cannot achieve high throughput screening and that conventional high throughput shaking tables cannot achieve microenvironment control in the culture vessel can be solved. The parallel bioreactor system according to the present invention can achieve parallel culture of a single variety of sample, and can also be used for culturing multiple different varieties of samples at the same time on one platform, and thus the parallel bioreactor system can be widely applied to high-expression cell clone screening, culture condition exploration, culture process optimization, culture medium optimization and other new product development processes of biological pharmacy.

Figure 1:
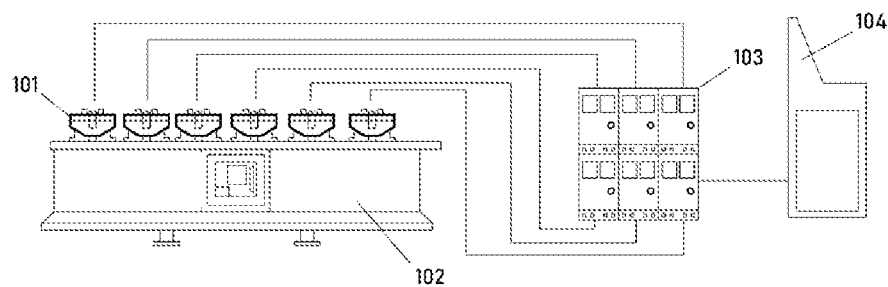
FIG. 1 shows a parallel bioreactor system according to an embodiment of the present invention.

The parallel bioreactor system according to the present invention mainly includes an oscillator, a plurality of culture vessels and a control system. FIG. 1 shows a parallel bioreactor system according to an embodiment of the present invention, including a plurality of culture vessels 101, an oscillator 102 and a control system. For example, the control system may include a master control console 104 and a plurality of reaction controllers 103.

For example, the master control console 104 can be a computer (an upper computer), which operates a control program and is provided with an input interface to receive the input of an operator. Preferably, the number of the reaction controllers 103 can be the same as the number of the culture vessels 101, and each reaction controller 103 is separately connected to and/or controls sensor(s) and actuator(s) associated with one corresponding culture vessel 101. Therefore, the parallel bioreactor system according to the present invention can independently control related operations of each culture vessel, which is particularly advantageous in the case that multiple different varieties of cells and/or microorganisms are cultured at the same time. Common parameters (e.g., a rotating speed of the oscillator or the like) of the culture vessels can be collectively controlled by the master control console 104. For example, the plurality of culture vessels can be divided into at least two groups, and different cells or microorganisms are cultured between each group of culture vessels. For example, the plurality of culture vessels are divided into a first group and a second group, first cells or microorganisms are cultured in the first group, and second cells or microorganisms are cultured in the second group.

The plurality of culture vessels are arranged on the same shaking plate and the parameters in each vessel can be independently controlled, therefore the system according to the present invention can carry out parallel culture of multiple candidate cell clones at one time under the same external environment and conditions, and the microenvironment in each culture vessel is controllable, thus providing a preferred platform for high throughput screening of stable and high-expression cell clones and culture process optimization. Similarly, the plurality of culture vessels are arranged on the same shaking plate and the parameters in each vessel can be independently controlled, therefore the system according to the present invention can carry out the parallel culture of one same sample or cell strain under the same external environment and conditions, and the microenvironment in each culture vessel is controllable, thus providing a preferred platform for sample/cell culture condition exploration and establishment, culture process optimization, culture medium optimization and accumulation of small amount of sample.

Figure 9:
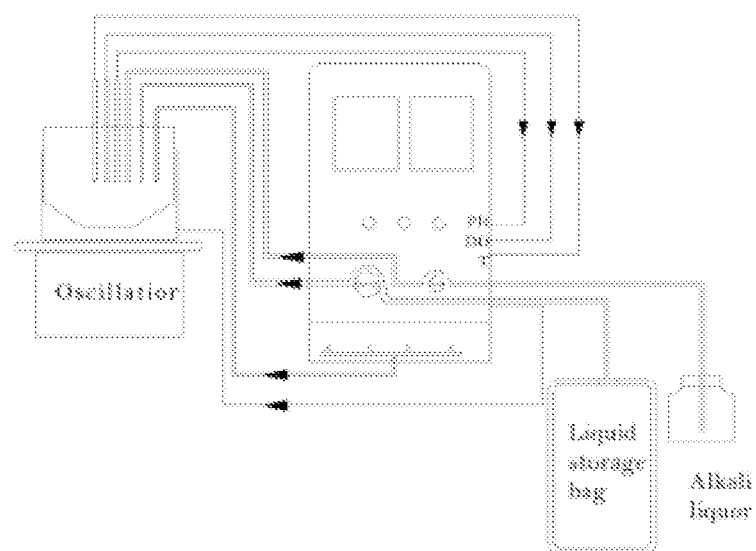
FIG. 9 shows a schematic connection diagram between a culture vessel and a reaction controller and the like according to an exemplary embodiment of the present invention.

FIG. 9 shows a schematic connection diagram between a culture vessel and a corresponding reaction controller and the like in an adherent culture mode (or attachment culture mode) according to an exemplary embodiment of the present invention. The connection between the culture vessel and the reaction controller thereof and the connection between the culture vessel, the reaction controller and other portions can be properly set according to culture needs.

Figure 2:
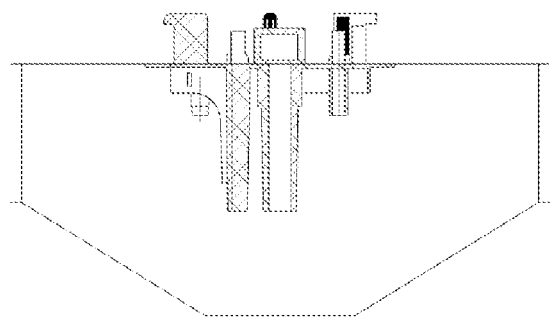
FIG. 2 shows a disposable culture bag according to an embodiment of the present invention.
Figure 3:
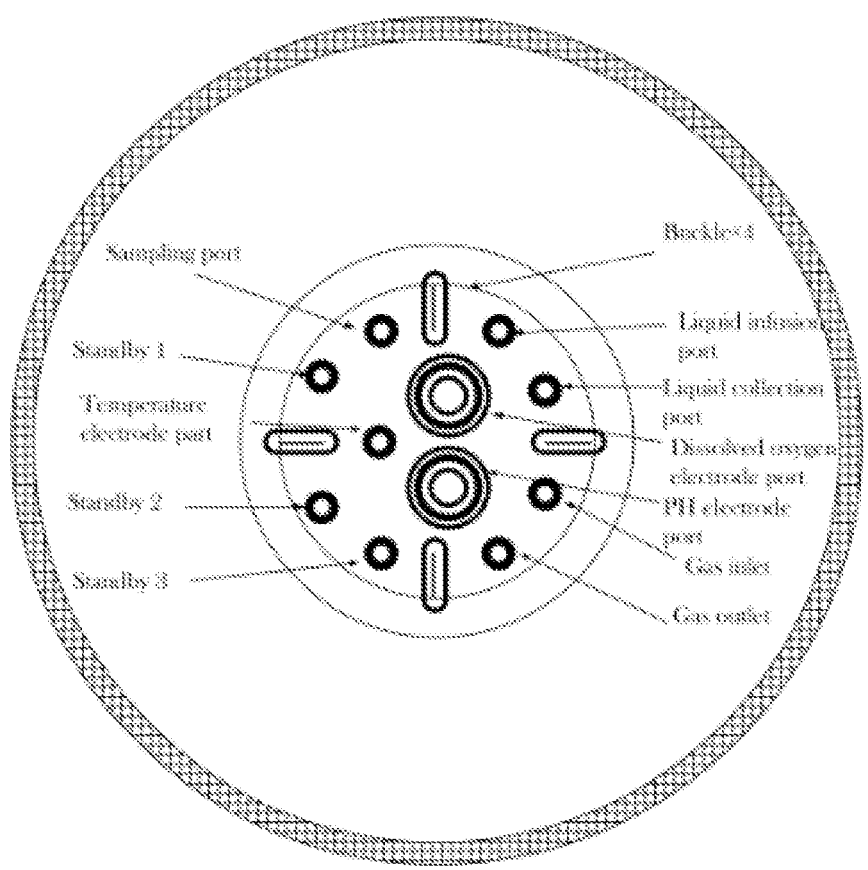
FIG. 3 shows a multifunctional cover plate according to an embodiment of the present invention.
Figure 4:
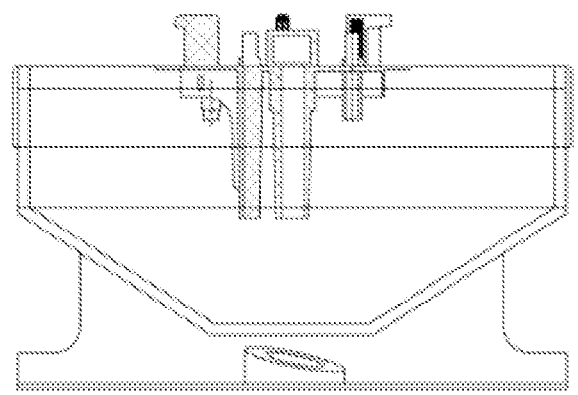
FIG. 4 shows a perspective view of a culture vessel, a disposable culture bag and a multifunctional cover plate that are assembled according to an embodiment of the present invention.

FIG. 2 shows a disposable culture bag according to an embodiment of the present invention. FIG. 3 shows a multifunctional cover plate according to an embodiment of the present invention. FIG. 4 shows a perspective view of a culture vessel, a disposable culture bag and a multifunctional cover plate that are assembled according to an embodiment of the present invention.

An inner cavity or a culture chamber is defined by an inner surface of a culture vessel 101 according to the present invention. As shown in FIG. 2, the inner cavity includes a cylindrical portion at an upper part and an inverted truncated conical bottom (or an inverted frustum-shaped bottom) at a lower part, a cross section of the cylindrical portion is consistent with the cross section of the top of the inverted truncated conical bottom, and the bottom of the cylindrical portion is joined with the top of the inverted truncated conical bottom. The cylindrical portion and the inverted truncated conical bottom are joined as an integral whole and have a common rotation axis, as shown in the figure.

The shape of an outer surface (or outer appearance) of the culture vessel 101 is not limited. Preferably, as shown in the figure, the outer appearance of the culture vessel corresponds to the shape of the inner cavity and includes a cylindrical portion at the upper part and an inverted truncated conical bottom at the lower part. In other embodiments, the shape of the outer surface of the culture vessel 101 can be a cylinder, a cone and the like, as long as it can be conveniently manufactured, stored, transported and mounted. In some embodiments, a portion used for fixing the culture vessel 101 to the oscillator can be arranged at the outside of the culture vessel 101, for example, a flange for passing through a bolt, etc.

Preferably, the culture vessel 101 is at least partially inserted in a culture vessel hole (or mounting hole) formed in the shaking plate, the shape of the culture vessel hole is matched with the outer shape of the culture vessel 101, so that the culture vessel 101 can be stably mounted on the shaking plate. The culture vessel 101 can be completely inserted in the culture vessel hole. Alternatively, the culture vessel is partially inserted in the culture vessel hole. For example, the culture vessel hole includes a cylindrical portion at the upper part and an inverted truncated conical bottom at the lower part, but the height of the cylindrical portion is less than the height of the cylindrical portion of the culture vessel. Or, the culture vessel hole can only include the inverted truncated conical bottom.

A disposable culture bag is arranged in a corresponding culture vessel according to the present invention. Preferably, the disposable culture bag is a flexible culture bag. In other embodiments, the disposable culture bag can also be made of a hard material. The disposable culture bag has a shape consistent with that of the inner cavity of the culture vessel (i.e., the appearance and the inner shape thereof are consistent with the shape of the inner cavity of the culture vessel). For example, when the disposable culture bag is the flexible culture bag, it has a smaller wall thickness, and the outer shape and the inner shape when unfolded are consistent with that of the inner cavity of the culture vessel.

That is to say, the unfolded disposable culture bag also includes a cylindrical portion at the upper part and an inverted truncated conical bottom (or an inverted frustum-shaped bottom) at the lower part, the cross section of the cylindrical portion is consistent with the cross section of the top of the inverted truncated conical bottom, and the bottom of the cylindrical portion is joined with the top of the inverted truncated conical bottom. The cylindrical portion and the inverted truncated conical bottom are joined as an integral whole and have a common rotation axis.

A diameter-height ratio of the inverted truncated conical bottom of the culture vessel of the present invention is greater than 1:1, so that a ratio of the superficial area of a culture medium in the culture vessel to the volume of the culture medium is greater than 0.14 $cm^2/cm^3$.

The culture vessel of the present invention has a flat bottom of an inverted truncated cone (the inverted truncated conical bottom), which is conducive to guiding the culture medium into the culture vessel, and the superficial area of the culture medium is obviously large, which is beneficial for the culture medium to contact an oxygen-containing gas in the vessel and also beneficial for the escape of the gas in the culture medium. Under the drive of the shaking plate of the oscillator, the culture medium can circularly brush the inner surface of the vessel to form a thin culture medium layer in a larger range, so as to further expand the superficial area of the culture medium, increase the throughput, improve the mixing, generate no shearing force or extremely small shearing force and generate extremely small mechanical stress.

According to the culture vessel of the present invention, the air can enter into the body of the culture vessel.

According to the culture vessel of the present invention, preferably, the taper angle of the cone body of the inverted truncated cone is 30°-70°. Since the angle of such range is adopted, the inoculation volume of seed cells or microorganisms in the vessel can be further reduced, so that a larger area of the culture medium is acquired in a culture process, and meanwhile a better mixing effect is obtained. Further, the cost can be further reduced, and higher application friendliness is achieved.

Figure 5:
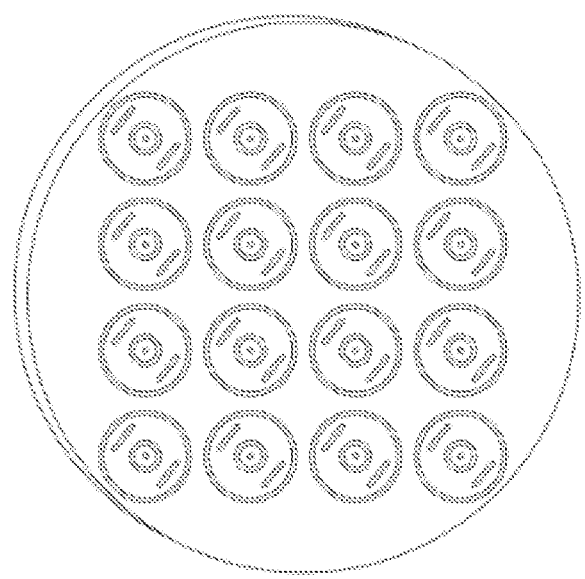
FIG. 5 shows multiple culture vessels mounted on a shaking plate according to an embodiment of the present invention.

Preferably, the volume of each culture vessel according to the present invention is in 0.3 L-5 L, the parameter control of each culture vessel can be controlled by independent control channels, and records, reports and other data management are relatively independent. FIG. 5 shows a plurality of culture vessels mounted on the shaking plate according to an embodiment of the present invention. The parallel bioreactor system according to the present invention can include up to 50 culture vessels. In FIG. 5, 16 culture vessels are provided and are mounted on the shaking plate in a rectangular array. According to other embodiments, the culture vessels can also be mounted on the shaking plate in an annular array. The plurality of culture vessels in the present invention have the same structures and features and are arranged on the shaking plate of the same oscillator, and thus the same external working parameters can be obtained.

Preferably, the culture vessel according to the present invention can be composed of glass, metal and other materials.

In a cell (or microorganism) culture process, various parameters in a cell growth environment must be monitored in real time, and the culture environment or conditions must be correspondingly monitored and changed according to the changes of the parameters. The traditional methods for monitoring the parameters of the cell culture environment is generally carried out by directly taking out cell culture solution to perform offline monitoring, or by fixedly placing each detection electrode at a certain fixed position in the cell culture vessel. Meanwhile, culture bag interfaces are different and cannot be universally applied to different types of cell culture, resulting in higher manufacturing and using costs.

According to the present invention, a multifunctional cover plate can be arranged at the top of the disposable culture bag. Preferably, the disposable culture bag and the multifunctional cover plate are integrated. For example, the culture bag is directly welded on the cover plate in a physical welding manner to constitute an integral component. Since the shape of the disposable culture bag after being inflated or filled with the culture solution (being unfolded) is consistent with that of the culture vessel, after being inflated or filled with the culture solution by a pipeline, the disposable culture bag can be firmly abutted to the culture vessel under the action of the gravity. Other restraining or fixing devices can also be set to keep the disposable culture bag if necessary.

Preferably, 6-12 connection holes are collectively formed in the cover plate, and the connection holes lead to the inside of the disposable culture bag and can be sealed by threads with good gas tightness. According to the needs of cell culture, any connection holes can be used for connecting to the detection electrodes to online monitor the temperature, the dissolved oxygen, the pH and other environmental parameters in the cell culture process. Or, conduits are connected through the connection holes to carry out cell culture inoculation, culture solution adding, sampling, recycling, harvest, gas change and other operations, so as to further optimize the culture conditions and improve the cell culture density. Meanwhile, the connection holes in the multifunctional cover plate that can be applied to various disposable culture bags may be thread interfaces using a unified standard, so that the gas tightness is good, and the connection holes can be used flexibly according to the needs of the cell culture. Unnecessary connection holes in a specific culture process can be sealed easily.

As shown in FIG. 3, 11 connection holes (interfaces) are formed in the multifunctional cover plate according to a preferred embodiment of the present invention, and can be sealed by threads with good gas tightness. The 11 connection holes are respectively standby holes 1-3, a sampling port, a temperature electrode port, a liquid infusion port, a liquid collection port, a DO (dissolved oxygen) electrode port, a pH electrode port, a gas inlet and a gas outlet, which can be flexibly used according to the needs of the cell culture and can be applied to various types of disposable culture bags.

FIG. 4 shows a perspective view of a culture vessel, a disposable culture bag and a multifunctional cover plate that are assembled according to an embodiment of the present invention. In the embodiment, the outer appearance of the culture vessel corresponds to the shape of the inner cavity and includes the cylindrical portion at the upper part and the inverted truncated conical bottom at the lower part. The outer appearance and the shape of the inner volume of the unfolded disposable culture bag are consistent with the shape of the inner cavity of the culture vessel. The multifunctional cover plate is arranged at the top of the disposable culture bag, and the multifunctional cover plate is provided with a plurality of connection holes.

Figure 6:
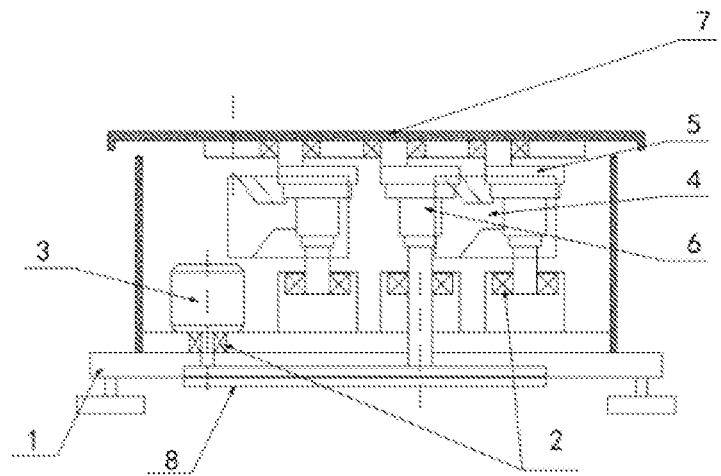
FIG. 6 shows a schematic diagram of an oscillator according to an embodiment of the present invention.

FIG. 6 shows a schematic diagram of an oscillator according to an embodiment of the present invention.

The oscillator according to present invention mainly includes a support and a shaking plate, and the shaking plate can generate oscillating motion relative to the support. In one embodiment, the oscillator further includes a motor, a main transmission eccentric shaft and supporting eccentric shafts. The main transmission eccentric shaft and the supporting eccentric shafts are fixed between the support and the shaking plate by bearings, and the motor is connected to the main transmission eccentric shaft through a belt. Four supporting eccentric shafts of the oscillator are evenly distributed at the bottom of the oscillator, and a balancing weight is mounted on each of the supporting eccentric shaft to play a support role. The balancing weight forms an angle of 180° with the eccentric direction to balance a centrifugal force generated by a load in an oscillating process of the oscillator. The shaking plate can carry out eccentric rotation about a vertical rotating center in the horizontal direction or plane, and since the shaking plate is supported by the four supporting eccentric shafts, the shaking plate can bear a very large load. Meanwhile, in the oscillating process of the oscillator, the supporting eccentric shafts are provided with the balancing weights to balance the load, and thus the oscillator body will generate no displacement. Under the drive of the motor, the shaking plate of the oscillator carries out rotary reciprocating horizontal oscillating motion, namely horizontal eccentric rotation, according to a set amplitude.

Figure 7:
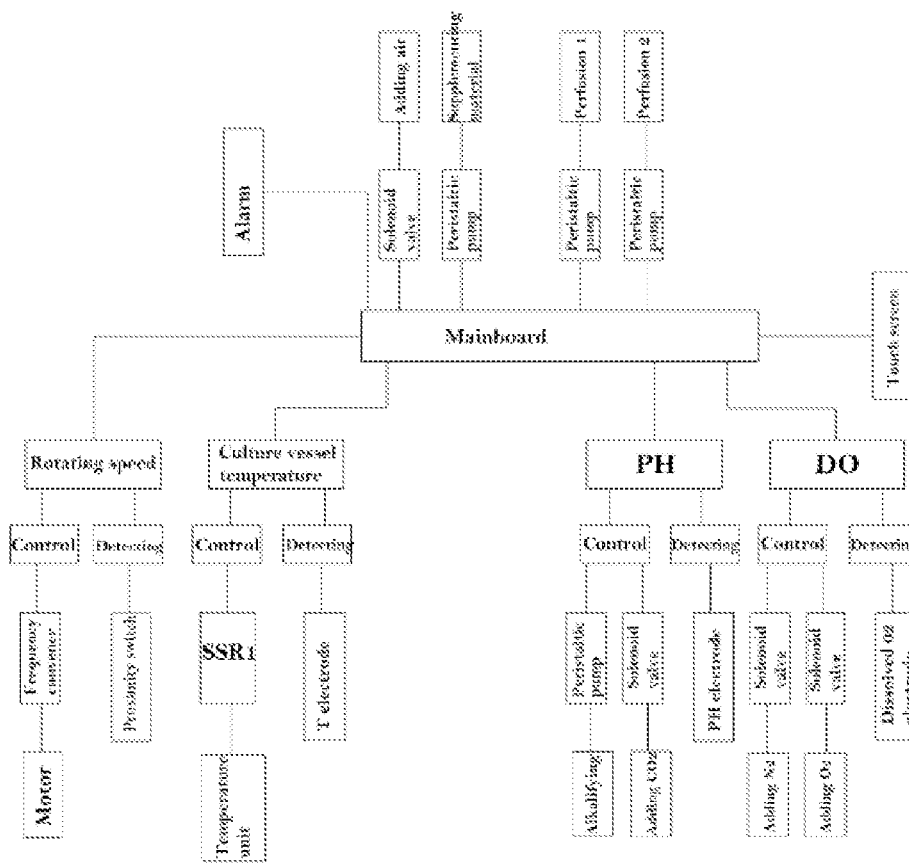
FIG. 7 shows exemplary layout of a control system according to the present invention.

As shown in FIG. 6, according to an embodiment of the present invention, the oscillator includes a support 1, bearings 2, a motor 3, a shaking plate 7, a main transmission eccentric shaft 6, supporting eccentric shafts 5 and balancing weights 4, wherein the supporting eccentric shafts 5 and the main transmission eccentric shaft are fixed on the support 1 by the bearings 2 and are connected to the shaking plate by the bearings, and the motor 3 is connected with the main transmission eccentric shaft 6 by a belt 8 to drive the main transmission eccentric shaft 6 to rotate. Since the main transmission eccentric shaft 6 is fixed on the support 1, the eccentric portion thereof is connected to the shaking plate 7 as shown in the figure, and therefore when the main transmission eccentric shaft 6 rotates, it drives the shaking plate 7 to carry out horizontal rotary oscillation about a vertical direction. FIG. 7 shows an exemplary layout of a control system according to the present invention.

The control system may include a main controller (e.g., a computer), a control circuit and an automatic control program. For example, the control circuit can include a variety of controllers, sensors, drives, connection pipelines and circuits. Usually, the control circuit can include a PLC (programmable logic controller), a touch screen, an electric control board, a peristaltic pump, a blower, a solenoid valve, a liquid level pump, an air pump, an electronic ruler, a rotating speed sensor, a DO (dissolved oxygen) transmitter, a PH transmitter, a T electrode, a frequency converter, an SF drive (servo driver), a relay, a heating film, etc. The electric control board is respectively connected with the peristaltic pump, the blower, the solenoid valve, the liquid level pump and the air pump, a PLC is respectively connected with the touch screen, the electric control board, the electronic ruler, the rotating speed sensor, the DO transmitter, the PH transmitter, the T electrode, the frequency converter, the SF driver and the relay, wherein the frequency converter controls the oscillator, the SF drive controls a perfusion lifting frame, and the relay controls the heating film.

The arrangement and connection of the control circuit according to the present invention can be adjusted according to the needs. For example, the sensors in the culture vessel can be connected through the connection holes of the multifunctional cover plate to obtain corresponding data. A culture solution input pipeline and the like can be connected to the culture vessel through the connection holes of the multifunctional cover plate, and the solenoid valve is arranged at a proper position to control the on/off of the pipelines. FIG. 3 shows an exemplary arrangement of the connection holes in the multifunctional cover plate, and corresponding control circuit arrangement can be seen. The control system according to the present invention can separately control each of the plurality of culture vessel, so related arrangements at each cover plate can be different from each other.

The control system has two operation modes, i.e. a manual control mode and an automatic control mode.

In the manual control mode, corresponding operations of the control system can be controlled through the upper computer, and the parameters in the culture vessel of the system are adjusted, so that the environment of the culture vessels is suitable for the culture needs of cells or microorganisms.

In the automatic control mode, the necessary parameters can be preset according to the culture needs of cells or microorganisms, and the system automatically adjusts the environment in the culture vessel in an automatic adjustment mode to meet the environment necessary for the free culture and growth of cultures.

According to the embodiment of the present invention, the automatic control of some parameters is described as follows.

Generally, calibration operation is needed before a temperature, a pH value or a dissolved oxygen signal is collected for the first time. At the same time, a harvest pump and a liquid infusion pump also need to be calibrated in order to make the volume of liquid in the culture vessel approximately maintain a balance.

1. Temperature Control

The temperature signal is converted by a PT100 transducer into a 4-20 mA current signal to enter an analog input channel of the control system. The control system automatically converts the 4-20 mA current signal into a corresponding temperature value. The control system compares the collected temperature value with a system set value. If the collected value is much smaller than the set value, a temperature heating valve is normally open. If a sampling value is less than the set value within a certain range, the control system carries out PMW mode control and periodically controls the on/off of an output heating valve. If the sampling value is greater than the set value, the heating valve is disconnected.

2. PH Value Control

A pH sensor converts the collected signal into the 4-20 mA current signal by the transducer and conveys the same to the analog input channel of the control system. The control system automatically converts the 4-20 mA current signal into a corresponding pH value.

1) Operation on a PH Upper Limit

If the collected value is far greater than the set value, then a CO2 valve is normally open. If the sampling value is greater than the set value within a certain range, the control system carries out the PWM mode control and periodically controls the on/off of an output CO2 valve. If the sampling value is less than the set value then the CO2 valve is disconnected.

2) Operation on a PH Lower Limit

If the collected value is far less than the set value, an alkali adding pump valve is normally open. If the sampling value is less than the set value within a certain range, the control system carries out the PWM mode control and periodically controls the on/off of an output alkali adding pump valve. If the sampling value is greater than the set value, then the alkali adding pump valve is disconnected.

3) The sampling value between the upper it and the lower limit of the pH

Neither of the CO2 valve and the alkali adding pump valve is opened.

3. Dissolved Oxygen Control

An oxygen content sensor converts the collected signal into the 4-20 mA current signal and conveys the same to the analog input channel of the control system. The control system automatically converts the current signal into a corresponding dissolved oxygen value.

1) Operation on a Dissolved Oxygen Upper Limit

If the collected value is far greater than the set value, then a N2 (nitrogen) filling valve is normally open. If the sampling value is greater than the set value within a certain range, the control system carries out the PWM mode control and periodically controls the on/off of an N2 output valve. If the sampling value is less than the set value, then the N2 valve is disconnected.

2) Operation on a Dissolved Oxygen Lower Limit If the collected value is far less than the set value, an O2 (oxygen) adding valve is normally open. If the sampling value is less than the set value within a certain range, the control system carries out the PWM mode control and periodically controls the on/off of an O2 output valve. If the sampling value is greater than the set value, then the O2 valve is disconnected.

3) If the Sampling Value is Between the Upper Limit and the Lower Limit of the Dissolved Oxygen Neither of the N2 valve and the O2 valve is opened.

4. Control of Harvest and Liquid Infusion of the System

In the cell culture process, the culture solution in the culture vessel is always consumed. The system needs to add a certain amount of culture solution regularly to the culture vessel to ensure the growth of the cells. In order to make the amount of liquid contained in the culture vessel basically unchanged, the amount of harvest and the amount of liquid infusion need to basically reach a balance, and this goal can be achieved by harvesting the culture solution by a system harvest pump while carrying out liquid infusion.

By setting the corresponding total liquid infusion amount or total harvest amount and the corresponding total time amount at one time, the system automatically calculates the time required for liquid infusion or harvest of the system within each minute. Therefore, the work of the corresponding liquid infusion pump or harvest pump can be controlled by the aforementioned PWM mode.

5. Setting and Control of a Shaking Table Rotating Speed

The system converts a given shaking table rotating speed signal to output through the analog output channel, and drives the motor to rotate according to the given rotating speed. In an operation process, the actual rotating speed of the system is detected by the input of a photoelectric detection switch. If the actual rotating speed deviates from the given rotating speed, the system will automatically adjust the rotating speed, so that the actual rotating speed is matched with the set rotating speed.

6. Alarm Output of the System

After upper and lower alarm limits of the temperature, the pH, the dissolved oxygen, the shaking table rotating speed and the like are set, if the actual parameter value of the system is greater than the upper alarm limit or less than the lower alarm limit, a system alarm signal is triggered, and a buzzer alarms. Meanwhile, the reason for triggering the alarm signal is displayed on the upper computer, so that the operator can conveniently check it.

7. Automatic Control Program of a Perfusion Servo System in the Case that the Perfusion System is Adopted (which will be described with Reference to FIG. 8)

a) Liquid Level Control of the Perfusion System

The liquid level of the perfusion system is controlled by a high and low level photoelectric detection switch, and when the liquid level of the system is between the high level and the low level, the motor of the perfusion system does not work. When a low level signal is detected, the perfusion motor infuses liquid so that the liquid level enters between the high level and the low level and continues operating for a certain period of time; and when a high level signal is detected, the perfusion motor discharges the liquid so that the liquid level enters between the high level and the low level and continues operating for a certain period of time. Therefore, the liquid level of the system is always located in a relatively stable liquid level area. The startups of perfusion liquid infusion and perfusion liquid discharge are interlocked.

b) Servo Motor Control of the Perfusion System

Zero point calibration needs to be carried out in the perfusion system at first, and after a lifting speed and a target position are set, an execution button is pressed, and the perfusion system moves towards the target position.

In the parallel bioreactor system according to the present invention, the plurality of culture vessels are arranged on the same oscillator shaking plate to carry out parallel culture of a single variety and can also be used for culturing multiple different varieties at the same time on one platform. Since the shaking plate of the oscillator collectively drives the culture vessels with the inverted truncated conical bottoms to shake, sufficient dissolved oxygen and a unified culture rate can be provided to support the growth of high-density cells. Accordingly, the high throughput screening and culture process optimization of high-expression cell clones can be achieved under high-density cell culture conditions. The entire culture process is high in efficiency, easy to operate and low in cost, and thus can be widely applied to high-expression cell clone screening, culture condition exploration, culture process optimization, culture medium optimization, seed chain amplification and other new product development processes of biological pharmacy.

According to the aforementioned embodiment of the present invention, since the plurality of culture vessels are provided and each culture vessel can be independently controlled, the problem that conventional reactors cannot achieve high throughput screening of samples or cell clones culture process optimization can be solved. According to the aforementioned embodiment of the present invention, since each culture vessel can be independently controlled, the problem that conventional high throughput shaking tables cannot achieve microenvironment control in the culture vessel can be solved.

According to the aforementioned embodiment of the present invention, since the shapes of the inner cavity of the culture vessel and the disposable culture bag are inverted truncated cones, the shearing force is extremely small in the cell culture, the dissolved oxygen level is high, and the growth density of cells or microorganisms sensitive to the shearing force can be effectively improved, thus providing a great potential of improvement for process optimization and culture medium optimization. According to the aforementioned embodiment of the present invention, since the plurality of culture vessels are arranged on the same shaking plate and the parameters in each culture vessel can be independently controlled, the parallel culture of multiple samples can be carried out at one time under the same external environment and conditions, and the microenvironment in each culture vessel is controllable, thus providing a preferred platform for high throughput screening of the samples, and particularly the high throughput screening of cell clones. According to the aforementioned embodiment of the present invention, the parallel culture of multiple candidate cell clones can be carried out at one time under the same external environment and conditions, and the microenvironment in each culture vessel is controllable, thus providing a preferred platform for the high throughput screening of stable and high-expression cell clones and culture process optimization. According to the aforementioned embodiment of the present invention, the parallel culture of one same sample or cell strain can be carried out under the same external environment and conditions, and the microenvironment in each culture vessel is controllable, and thus providing a preferred platform for sample/cell culture condition exploration and establishment, culture process optimization, culture medium optimization and accumulation of small amount of sample.

Figure 8:
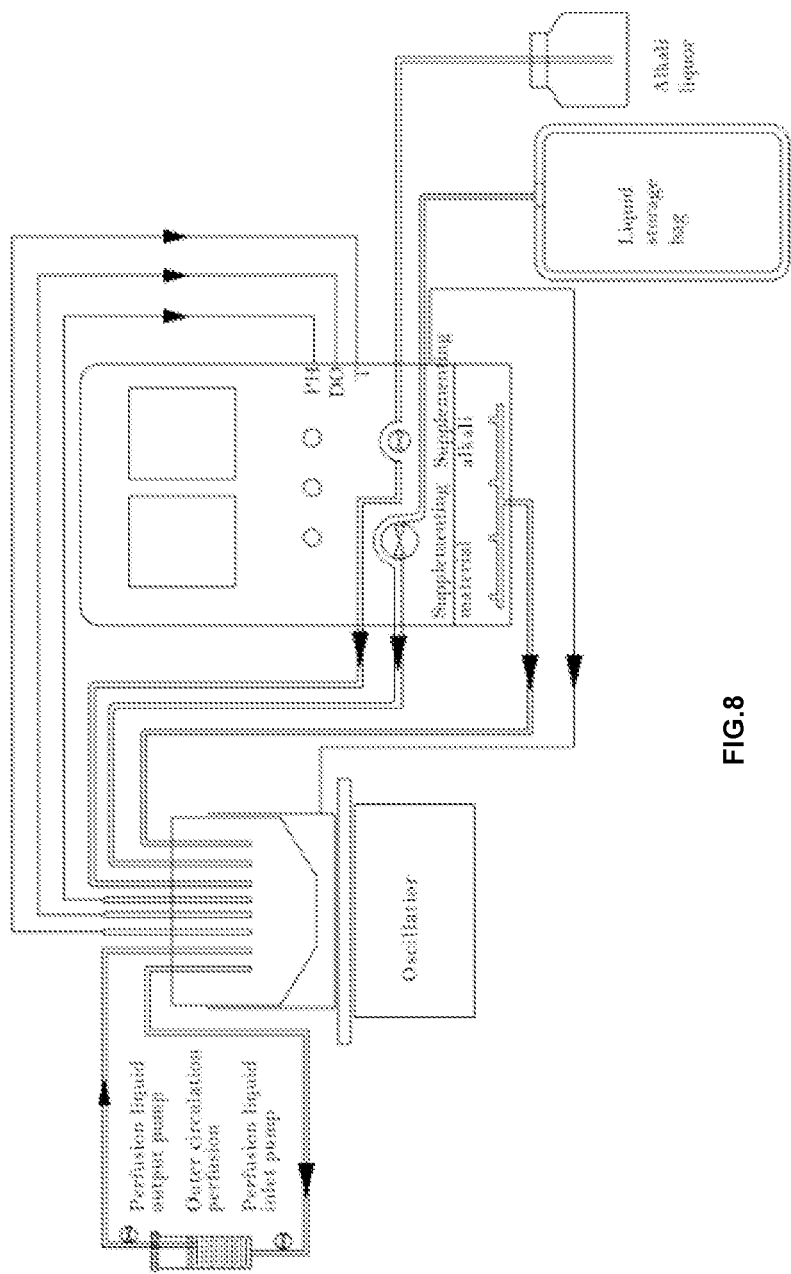
FIG. 8 shows an exemplary working principle of a perfusion system according to the present invention.

FIG. 8 shows an exemplary working principle of a perfusion system according to the present invention.

As a further solution, a perfusion system used for culturing specific cells or microorganisms is mounted on the parallel bioreactor system according to the present invention. The perfusion system mainly includes a bracket, bracket lifting adjusting buttons, a peristaltic pump, guide posts, a manual adjusting wheel and a perfusion culture bag vessel. The perfusion culture bag vessel is fixed between two guide posts on the bracket through fixing frames, the bracket lifting adjusting button is arranged at the lower ends of the guide posts, the peristaltic pump is fixed in a cabinet, and the manual adjusting wheel is fixed on a movable plate on the guide posts.

When the perfusion system is used for culturing specific cells or microorganisms, the culture vessel provides the dissolved oxygen and the culture solution, and the pH, the temperature and other conditions suitable for cell growth are adjusted and controlled online. The culture solution is injected into the perfusion culture bag at a controllable flow rate and flows back into the culture vessel at a controllable flow rate under the action of the gravity, so as to form an outer circulation type perfusion culture mode. A culture carrier is fixed in the perfusion culture bag, and adherent cells or microorganisms are adsorbed on the culture carrier to grow. The culture solution flows by the carrier to provide nutrients necessary for the cultures and take away metabolites, so as to form a stable fluid environment on the surrounding of the cultures and provide a three-dimensional structure of growth, interflow and cell clusters formation, so as to achieve the purpose of high-density cell culture.

The present invention is not limited to the aforementioned specific description, and any modifications that are conceivable to those skilled in the art on the basis of the aforementioned description fall within the scope of the present invention.

The invention claimed is:

1. A culture method for culturing cells and/or microorganisms comprising:
    providing a parallel bioreactor system comprising:
        an oscillator for generating oscillating motion;
        a plurality of culture vessels mounted on the oscillator, wherein each culture vessel is provided with an inner cavity;
        disposable culture bags arranged in the inner cavities of the culture vessels and used for accommodating a culture solution;
        a support and a shaking plate, wherein the shaking plate generates the oscillating motion relative to the support, and the culture vessels are mounted on the same shaking plate; and
        wherein the oscillator consists of a motor, a main transmission eccentric shaft and four supporting eccentric shafts, the main transmission eccentric shaft and the four supporting eccentric shafts are connected between the support and the shaking plate by bearings, the motor drives the main transmission eccentric shaft and thus drives the shaking plate to carry out eccentric rotation about a vertical rotating center in the horizontal oscillating motion according to a set amplitude;
        a control system, wherein the control system controls the oscillating motion of the oscillator and parameters of the culture solution in each of the disposable culture bags, wherein the control system includes a master control console and a plurality of reaction controllers, the master control console controls the motion of the oscillator and each reaction controller is connected to the corresponding culture vessel to receive the parameters from each of the disposable culture bags and carry out related operations on the culture vessel; and independently monitoring and controlling each culture bags through the control system, wherein each of the four supporting eccentric shafts is evenly distributed on the bottom of the oscillator, a balancing weight is mounted on each supporting eccentric shaft, and the balancing weight forms an angle of 180° with the eccentric direction to balance a centrifugal force generated by a load in an oscillating process of the oscillator.

2. The culture method of claim 1, comprising:

dividing the plurality of culture bags into at least two groups;

culturing identical or different cells or microorganisms in each group of culture bags; and controlling the groups of culture bags to have different culture parameters there between.

3. The culture method of claim 1, wherein the inner cavity comprises a cylindrical portion at the upper part and an inverted truncated conical bottom at the lower part, a cross section of the cylindrical portion is consistent with the cross section of the top of the inverted truncated conical bottom, and the bottom of the cylindrical portion is joined with the top of the inverted truncated conical bottom.

4. The culture method of claim 1, wherein each disposable culture bag is provided with a multifunctional cover plate, and the multifunctional cover plate is connected to the top of the culture bag to seal the culture bag, and is provided with a plurality of connection holes leading to interior of the disposable culture bag.

5. The culture method of claim 1, wherein a diameter-height ratio of the inverted truncated conical bottom is greater than 1:1, and the taper angle of the inverted truncated conical bottom is within a range of 30°-70°.

6. The culture method of claim 1, wherein the disposable culture bag is a flexible culture bag.

7. The culture method of claim 6, wherein the flexible culture bag has a shape corresponding to that of the inner cavity of the culture vessel when being unfolded.

8. The culture method of claim 1, wherein the outer shape of the culture vessel corresponds to the shape of the inner cavity, and comprises a cylindrical portion at the upper part and an inverted truncated conical bottom at the lower part.

9. The culture method of claim 1, wherein the shaking plate comprises a plurality of culture vessel holes, and each of the culture vessel holes has a shape matched with the outer shape of the culture vessels so as to at least partially accommodate one culture vessel.

10. The culture method of claim 4, wherein the connection holes of the multifunctional cover plate are suitable for being connected with a detection electrode or a conduit.

11. The culture method of claim 1, the parallel bioreactor system further comprises a perfusion system, wherein the perfusion system comprises a bracket having two guide posts and a perfusion type culture bag vessel fixed between the two guide posts, and lifting adjustment buttons are arranged at lower ends of the guide posts.

12. The culture method of claim 11, wherein the perfusion type culture bag vessel is connected with the culture vessel through pipelines and the connection holes of the multifunctional cover plate to form an outer circulation type perfusion culture mode.

13. The culture method of claim 1, wherein contorting one or more of the following parameters in the disposable culture bag disposed in the culture vessel by the control system: liquid level, temperature, pH value or dissolved oxygen level.

* * * * *